(12) United States Patent
Powell et al.

(10) Patent No.: US 8,313,527 B2
(45) Date of Patent: Nov. 20, 2012

(54) SOFT PROSTHESIS SHELL TEXTURING METHOD

(75) Inventors: Thomas E. Powell, Santa Barbara, CA (US); Loantrang Dang, Ventura, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 12/261,939

(22) Filed: Oct. 30, 2008

(65) Prior Publication Data

US 2009/0118829 A1 May 7, 2009

Related U.S. Application Data

(60) Provisional application No. 60/985,489, filed on Nov. 5, 2007, provisional application No. 60/991,004, filed on Nov. 29, 2007.

(51) Int. Cl.
*A61F 2/12* (2006.01)
*A61F 2/02* (2006.01)

(52) U.S. Cl. ........................ 623/8; 623/23.74

(58) Field of Classification Search ........ 623/8, 23.72–23.76; 427/2.24
See application file for complete search history.

(56) References Cited

U.S. PATENT DOCUMENTS

| | | |
|---|---|---|
| 2,805,208 A | 9/1957 | Roche |
| 3,189,921 A | 6/1965 | Pangman |
| 3,293,663 A | 12/1966 | Cronin |
| 3,366,975 A | 2/1968 | Pangman |
| 3,559,214 A | 2/1971 | Pangman |
| 3,665,520 A | 5/1972 | Perras |
| 3,852,832 A | 12/1974 | McGhan |
| 3,934,274 A | 1/1976 | Hartley, Jr. |
| 4,157,085 A | 6/1979 | Austad |
| 4,231,979 A | 11/1980 | White |
| 4,264,990 A | 5/1981 | Hamas |
| 4,298,997 A | 11/1981 | Rybka |
| 4,298,998 A | 11/1981 | Naficy |
| 4,329,385 A | 5/1982 | Banks |
| 4,428,082 A | 1/1984 | Naficy |
| 4,433,440 A | 2/1984 | Cohen |
| 4,470,160 A | 9/1984 | Cavon |

(Continued)

FOREIGN PATENT DOCUMENTS

EP 0315814 5/1989

(Continued)

OTHER PUBLICATIONS

Alvarez, Sonia et al., "Synthesis of Macro/Mesoporous Silica and Carbon Monoliths by Using a Commercial Polyurethane Foam as Sacrificial Template", Materials Letters, 61, 2378-2381 (2007).

(Continued)

*Primary Examiner* — David Isabella
*Assistant Examiner* — Andrew Iwamaye
(74) *Attorney, Agent, or Firm* — Linda Fox; Stephen Donovan; Debra Condino

(57) ABSTRACT

A method of texturing a soft prosthetic implant shell, such as a silicone breast implant shell. A soft prosthetic implant with a textured external surface layer of silicone elastomer and having an open-cell structure is made by adhering and then dissolving round salt crystals. The resulting roughened surface has enhanced physical properties relative to surfaces formed with angular salt crystals. An implant having such a textured external surface layer is expected to help prevent capsular contraction, to help prevent scar formation, and to help in anchoring the implant within the body.

12 Claims, 6 Drawing Sheets

U.S. PATENT DOCUMENTS

| | | |
|---|---|---|
| 4,482,577 A | 11/1984 | Goldstein |
| 4,499,211 A | 2/1985 | Walch |
| 4,531,244 A | 7/1985 | Hamas |
| 4,573,999 A | 3/1986 | Netto |
| 4,592,755 A | 6/1986 | Penton |
| 4,610,690 A | 9/1986 | Tiffamy |
| 4,636,213 A | 1/1987 | Pakiam |
| 4,643,733 A | 2/1987 | Becker |
| 4,648,880 A | 3/1987 | Brauman |
| 4,650,487 A | 3/1987 | Chaglassian |
| 4,651,717 A | 3/1987 | Jakubczak |
| 4,681,587 A | 7/1987 | Eberl |
| 4,740,208 A | 4/1988 | Cavon |
| 4,772,285 A | 9/1988 | Ksander |
| 4,773,908 A | 9/1988 | Becker |
| 4,773,909 A | 9/1988 | Chaglassian |
| 4,790,848 A | 12/1988 | Cronin |
| 4,795,464 A | 1/1989 | Eberl |
| 4,803,025 A | 2/1989 | Brockmeyer |
| 4,828,560 A | 5/1989 | Heyler |
| 4,841,992 A | 6/1989 | Sasaki |
| 4,859,383 A | 8/1989 | Dillon |
| 4,859,712 A | 8/1989 | Cox |
| 4,889,744 A | 12/1989 | Quaid |
| 4,899,764 A | 2/1990 | Gauger |
| 4,902,294 A | 2/1990 | Gosserez |
| 4,906,423 A | 3/1990 | Frisch |
| 4,936,858 A | 6/1990 | O'Keeffe |
| 4,944,749 A | 7/1990 | Becker |
| 4,944,750 A | 7/1990 | Cox, Jr. |
| 4,950,292 A | 8/1990 | Audretsch |
| 4,955,907 A | 9/1990 | Ledergerber |
| 4,955,909 A | 9/1990 | Ersek |
| 4,960,425 A | 10/1990 | Yan |
| 4,963,150 A | 10/1990 | Brauman |
| 4,965,430 A | 10/1990 | Curtis |
| 4,969,899 A | 11/1990 | Cox, Jr. |
| 5,002,572 A | 3/1991 | Picha |
| 5,007,929 A | 4/1991 | Quaid |
| 5,007,940 A | 4/1991 | Berg |
| 5,022,942 A | 6/1991 | Yan |
| 5,026,394 A | 6/1991 | Baker |
| 5,034,422 A | 7/1991 | Triolo |
| 5,035,249 A | 7/1991 | Sasaki |
| 5,092,348 A | 3/1992 | Dubrul |
| 5,092,882 A | 3/1992 | Lynn |
| 5,104,409 A | 4/1992 | Baker |
| 5,116,387 A | 5/1992 | Berg |
| 5,135,959 A | 8/1992 | Hill |
| 5,146,933 A | 9/1992 | Boyd |
| 5,147,398 A | 9/1992 | Lynn |
| 5,158,571 A | 10/1992 | Picha |
| 5,158,573 A | 10/1992 | Berg |
| 5,171,269 A | 12/1992 | Bark |
| 5,185,297 A | 2/1993 | Park |
| 5,207,709 A | 5/1993 | Picha |
| 5,236,453 A | 8/1993 | Picha |
| 5,236,454 A | 8/1993 | Miller |
| 5,236,457 A | 8/1993 | Devanathan |
| 5,282,856 A | 2/1994 | Ledergerber |
| 5,296,069 A | 3/1994 | Robert |
| 5,348,788 A | 9/1994 | White |
| 5,354,338 A | 10/1994 | Ledergerber |
| 5,358,521 A | 10/1994 | Shane |
| 5,376,117 A | 12/1994 | Pinchuk |
| 5,383,929 A | 1/1995 | Ledergerber |
| 5,437,824 A | 8/1995 | Carlisle |
| 5,441,919 A | 8/1995 | Park |
| 5,447,535 A | 9/1995 | Muller |
| 5,455,100 A | 10/1995 | White |
| 5,480,430 A | 1/1996 | Carlisle |
| 5,496,367 A | 3/1996 | Fisher |
| 5,496,370 A | 3/1996 | Hamas |
| 5,507,808 A | 4/1996 | Becker |
| 5,522,896 A | 6/1996 | Prescott |
| 5,525,275 A | 6/1996 | Iversen |
| 5,534,023 A | 7/1996 | Henley |
| 5,545,217 A | 8/1996 | Offray |
| 5,545,220 A | 8/1996 | Andrews |
| 5,549,671 A | 8/1996 | Waybright |
| 5,571,179 A | 11/1996 | Manders |
| 5,589,176 A | 12/1996 | Seare |
| 5,605,693 A | 2/1997 | Seare |
| 5,607,473 A | 3/1997 | Weber-Unger |
| 5,624,674 A | 4/1997 | Seare, Jr. |
| 5,630,843 A | 5/1997 | Rosenberg |
| 5,630,844 A | 5/1997 | Dogan |
| 5,653,755 A | 8/1997 | Ledergerber |
| 5,658,330 A | 8/1997 | Carlisle |
| 5,674,285 A | 10/1997 | Quaid |
| 5,681,572 A | 10/1997 | Seare, Jr. |
| 5,779,734 A | 7/1998 | Ledergerber |
| 5,798,065 A | 8/1998 | Picha |
| 5,824,081 A | 10/1998 | Knapp |
| 5,843,189 A | 12/1998 | Perouse |
| 5,855,588 A | 1/1999 | Young |
| 5,871,497 A | 2/1999 | Young |
| 5,895,423 A | 4/1999 | Becker |
| 5,935,164 A | 8/1999 | Iversen |
| 5,961,552 A | 10/1999 | Iversen |
| 5,964,803 A | 10/1999 | Iversen |
| 5,965,076 A | 10/1999 | Banks |
| 5,984,943 A | 11/1999 | Young |
| 6,071,309 A | 6/2000 | Knowlton |
| 6,074,421 A | 6/2000 | Murphy |
| 6,083,262 A | 7/2000 | Caravel |
| 6,099,565 A | 8/2000 | Sakura |
| 6,113,634 A | 9/2000 | Weber-Unger |
| 6,146,418 A | 11/2000 | Berman |
| 6,183,514 B1 | 2/2001 | Becker |
| 6,187,043 B1 | 2/2001 | Ledergerber |
| 6,203,570 B1 | 3/2001 | Baeke |
| 6,206,930 B1 | 3/2001 | Burg |
| 6,214,045 B1 | 4/2001 | Corbitt, Jr. |
| 6,214,926 B1 | 4/2001 | Winn |
| 6,315,796 B1 | 11/2001 | Eaton |
| 6,387,133 B1 | 5/2002 | Perouse |
| 6,432,138 B1 | 8/2002 | Offray |
| 6,464,726 B1 | 10/2002 | Heljenek |
| 6,520,989 B1 | 2/2003 | Eaton |
| 6,531,523 B1 | 3/2003 | Davankov |
| 6,544,287 B1 | 4/2003 | Johnson |
| 6,605,116 B2 | 8/2003 | Falcon |
| 6,638,308 B2 | 10/2003 | Corbitt, Jr. |
| 6,673,285 B2 | 1/2004 | Ma |
| 6,692,527 B1 | 2/2004 | Bellin |
| 6,755,861 B2 | 6/2004 | Nakao |
| 6,802,861 B1 | 10/2004 | Hamas |
| 6,811,570 B1 | 11/2004 | Gehl |
| 6,818,673 B2 | 11/2004 | Ferguson |
| 6,875,233 B1 | 4/2005 | Turner |
| 6,881,226 B2 | 4/2005 | Corbitt, Jr. |
| 6,900,055 B1 * | 5/2005 | Fuller et al. .................. 435/395 |
| 6,913,626 B2 | 7/2005 | McGhan |
| 6,916,339 B1 | 7/2005 | Missana |
| 6,921,418 B2 | 7/2005 | Ledergerber |
| 6,932,840 B1 | 8/2005 | Bretz |
| 7,105,116 B2 | 9/2006 | Bellin et al. |
| 7,169,180 B2 | 1/2007 | Brennan |
| 7,192,450 B2 | 3/2007 | Brauker et al. |
| 7,244,270 B2 | 7/2007 | Lesh |
| 7,323,208 B2 | 1/2008 | Ma et al. |
| 7,520,896 B2 | 4/2009 | Benslimane |
| 7,547,393 B2 | 6/2009 | Ramaswamy et al. |
| 7,625,405 B2 | 12/2009 | Purkait |
| 7,632,228 B2 | 12/2009 | Brauker et al. |
| 7,632,291 B2 | 12/2009 | Stephens |
| 7,641,688 B2 | 1/2010 | Lesh |
| 7,645,475 B2 | 1/2010 | Prewett |
| 2002/0038147 A1 | 3/2002 | Miller |
| 2002/0193885 A1 | 12/2002 | Legeay |
| 2003/0036803 A1 | 2/2003 | McGhan |
| 2003/0093151 A1 | 5/2003 | Zhang |
| 2003/0205846 A1 | 11/2003 | Bellin et al. |
| 2003/0208269 A1 | 11/2003 | Eaton |
| 2004/0010225 A1 | 1/2004 | Schuessler |
| 2004/0115241 A1 | 6/2004 | Calhoun |

| | | | |
|---|---|---|---|
| 2004/0127985 A1 | 7/2004 | Bellin | |
| 2004/0143327 A1 | 7/2004 | Ku | |
| 2004/0148024 A1 | 7/2004 | Williams | |
| 2004/0153151 A1 | 8/2004 | Gonzales | |
| 2004/0213986 A1 | 10/2004 | Kim | |
| 2005/0055093 A1 | 3/2005 | Brennan | |
| 2005/0070124 A1 | 3/2005 | Miller | |
| 2005/0112169 A1* | 5/2005 | Brauker et al. | 424/423 |
| 2005/0196452 A1 | 9/2005 | Boyan et al. | |
| 2005/0216094 A1* | 9/2005 | Prewett | 623/23.74 |
| 2006/0036320 A1 | 2/2006 | Job | |
| 2006/0136056 A1 | 6/2006 | Wohl | |
| 2006/0224239 A1 | 10/2006 | Tiahrt | |
| 2006/0229721 A1 | 10/2006 | Ku | |
| 2006/0235094 A1 | 10/2006 | Habibi-Naini | |
| 2006/0246121 A1 | 11/2006 | Ma | |
| 2007/0093911 A1 | 4/2007 | Fricke | |
| 2007/0104693 A1 | 5/2007 | Quijano | |
| 2007/0104695 A1 | 5/2007 | Quijano | |
| 2007/0116735 A1 | 5/2007 | Calhoun | |
| 2007/0135916 A1 | 6/2007 | Maxwell | |
| 2007/0154525 A1 | 7/2007 | Calhoun | |
| 2007/0190108 A1 | 8/2007 | Datta et al. | |
| 2008/0009830 A1 | 1/2008 | Fujimoto et al. | |
| 2008/0071371 A1* | 3/2008 | Elshout | 623/8 |
| 2008/0075752 A1 | 3/2008 | Ratner | |
| 2008/0241212 A1 | 10/2008 | Moses | |
| 2008/0268019 A1 | 10/2008 | Badylak et al. | |
| 2008/0312739 A1 | 12/2008 | Agerup | |
| 2009/0045166 A1 | 2/2009 | Li | |
| 2009/0082864 A1 | 3/2009 | Chen | |
| 2009/0087641 A1 | 4/2009 | Favis et al. | |
| 2009/0093878 A1 | 4/2009 | Glicksman | |
| 2009/0118829 A1 | 5/2009 | Powell et al. | |
| 2009/0125107 A1 | 5/2009 | Maxwell | |
| 2009/0169716 A1 | 7/2009 | Linhardt | |
| 2009/0198331 A1 | 8/2009 | Kesten et al. | |
| 2009/0198332 A1 | 8/2009 | Becker | |
| 2009/0198333 A1 | 8/2009 | Becker | |
| 2010/0042211 A1 | 2/2010 | VanEpps et al. | |
| 2011/0035004 A1 | 2/2011 | Maxwell | |

FOREIGN PATENT DOCUMENTS

| | | | |
|---|---|---|---|
| JP | 2003-062062 | 4/2003 | |
| JP | 2007-029717 | 8/2007 | |
| WO | WO 98/10803 | 3/1998 | |
| WO | WO00/24437 A2 | 5/2000 | |
| WO | WO 2004/037318 | 5/2004 | |
| WO | WO 2004/062531 | 7/2004 | |
| WO | WO 2009/061672 | 5/2009 | |
| WO | WO 2009/110917 | 9/2009 | |
| WO | WO 2011/094155 | 8/2011 | |
| WO | WO 2011/097499 | 8/2011 | |

OTHER PUBLICATIONS

Barr, S. et al., "Current Implant Surface Technology: An Examination of Their Nanostructure and Their Influence on Fibroblast Alignment and Biocompatibility", Elastic, 2009, 9, 198-217.

Barnsley, Philip et al., "Textured Surface Breast Implants in the Prevention of Capsular Contracture Among Breast Augmentation Patients: A Meta-Analysis of Randomized Controlled Trials", Plastic and Reconstructive Surgery, 2006, 117(7), 2182-2190.

Ma, Peter, "Scaffolds for tissue fabrication", Materials Today, 2004, 7, 30-40.

Mikes, Antonius et al., "Formation of Highly Porous Biodegradable Scaffolds for Tissue Engineering", Electronic Journal of Biotechnology, 2000, 3(2), 114-119.

Minami, Eliza et al., "The Composition and Behavior of Capsules Around Smooth and Textured Breast Implants in Pigs", Plastic and Reconstructive Surgery, 2006, 118940, 874-884.

Murphy, William et al., "Salt Fusion: An Approach to Improve Pore Interconnectivity Within Tissue Engineering Scaffolds", Tissue Engineering, vol. 8, Iss. 1, 2004.

Wei, Guobao et al., "Macroporous and Nanofibers Polymer Scaffolds and Polymer/bone-like Apatite Composite Scaffolds Generated by Sugar Spheres", Journal of Biomedical Materials Research Part A, 2006, 306-315.

Zhang, Yuan et al., "Macroporous Alumina Monoliths Prepared by Filling Polymer Foams With Alumina Hydrosols", J. Mater Sci., 44, 931-938 (2009).

Brauker et al., "Neovascularization of synthetic membranes directed by membrane microarchitecture", Journal of Biomedical Materials Research, vol. 29, pp. 1517-1524, 1995.

Sharkawy et al., "Engineering the tissue which encapsulates subcutaneous implants. II. Plasma-tissue exchange properties", 1998, pp. 586-597, John Wiley & Sons, Inc.

Brohim et al., "Early Tissue Reaction to Textured Breast Implant Surfaces", 1992, pp. 354-362, Little, Brown, and Company.

* cited by examiner

SOFT PROSTHESIS SHELL TEXTURING METHOD

RELATED APPLICATIONS

This application claims priority to U.S. Provisional Patent Application Ser. No. 60/985,489 filed on Nov. 5, 2007 and U.S. Provisional Patent Application Ser. No. 60/991,004 filed on Nov. 29, 2007 and each of which is incorporated herein by reference.

FIELD OF THE INVENTION

The present invention relates to soft prosthetic implants and, more particularly, to methods of texturing the exterior surface of such implants, for instance breast implants, to produce an open-cell texture on the outer surface.

BACKGROUND OF THE INVENTION

Implantable prostheses are commonly used to replace or augment body tissue. In the case of breast cancer, it is sometimes necessary to remove some or all of the mammary gland and surrounding tissue, which creates a void that can be filled with an implantable prosthesis. The implant serves to support surrounding tissue and to maintain the appearance of the body. The restoration of the normal appearance of the body has an extremely beneficial psychological effect on post-operative patients, eliminating much of the shock and depression that often follows extensive surgical procedures. Implantable prostheses are also used more generally for restoring the normal appearance of soft tissue in various areas of the body, such as the buttocks, chin, calf, etc.

Soft implantable prostheses typically include a relatively thin and quite flexible envelope or shell made of vulcanized (cured) silicone elastomer. The shell is filled either with a silicone gel or with a normal saline solution. The filling of the shell takes place before or after the shell is inserted through an incision in the patient.

The development of implants having textured outer surfaces reflects an attempt to prevent the contraction of the fibrous outer capsule that forms around the implant, which tends to render an implant spherical, painful and aesthetically undesirable. Layers of polyether, polyester or polyurethane foam material have been applied to the back sides of mammary prostheses so that fibrous-tissue could grow into the material and thereby anchor prosthesis securely to the chest wall. However, possible problems exist with foam materials, which may degrade in the body over a period of time, and the effectiveness of these materials for preventing capsular contracture may disappear as they degrade.

Despite many advances in the construction of soft prosthetic implants, there remains a need for better methods for texturing surfaces of implants.

SUMMARY OF THE INVENTION

The present invention provides processes for forming soft prosthetic implants having textured surfaces and implants formed by said processes. The processes generally comprise the steps of forming a flexible shell, adhering on the exterior of the flexible shell a distribution of rounded particles, curing the flexible shell with the rounded particles adhered thereto, and causing or allowing the rounded particles to be removed from the shell thereby leaving impressions of the particles in the shell to create an open-pored structure on a surface thereof.

In one embodiment, the flexible shell is formed of a silicone elastomer. For instance, the flexible shell may be formed of a plurality of layers of different silicone elastomers, or the flexible shell may be formed of a single homogeneous layer of a silicone elastomer.

The step of forming the flexible shell may comprise dipping a mandrel into a liquid dispersion of elastomeric material. Alternatively, the step of forming comprises rotational molding.

In one embodiment, the step of adhering comprises dipping the flexible shell into a liquid containing the rounded particles, for example, a liquid dispersion or emulsion of rounded particles, for example, rounded salt crystals. Prior to the step of dipping the flexible shell, the process may also include applying a tack coat layer onto the flexible shell.

In one aspect, the rounded particles comprise rounded crystals of sodium chloride and the solvent is an aqueous composition, for example, water. In other embodiments, the rounded particles comprise rounded sugar particles. In other embodiments, the rounded particles comprise a suitable solid material which is provided in a rounded particulate form, and which is capable of being adhered to a shell, for example, an uncured elastomer shell, and is capable of being dissolved, for example, using a solvent, thereby leaving open, rounded pores in the shell.

In one embodiment, the rounded particles used in accordance with the invention have a substantially uniform particle size of between about 150 microns and about 1450 microns. More specifically, the particles have a maximum particle size range selected from a group of ranges consisting of (1) a range between about 180 microns and about 425 microns, (2) a range between about 425 microns and about 850 microns, and (3) a range between about 850 microns and about 1450 microns. In one embodiment, about 90% of the particles are in the selected particle size range.

Another aspect of the invention is a soft prosthetic breast implant, formed by a process comprising the steps of forming a flexible shell of silicone elastomer in the shape of a breast implant, adhering on the exterior of the flexible shell a substantially even distribution of rounded particles, curing the flexible shell with the rounded particles adhered thereto, and exposing the flexible shell to a suitable solvent for a sufficient amount of time to dissolve the rounded particles thereby forming an open-pored structure on the exterior of the flexible shell.

In one embodiment, at least one, for example, at least two, for example all three of the physical properties of ultimate break force, ultimate elongation, and ultimate tensile strength of an implant formed in accordance with the present process is superior to an implant made using substantially the same process and the same materials except for conventional angular or non-rounded salt crystals instead of rounded salt crystals.

The step of forming the flexible shell may comprise dipping a mandrel into a liquid dispersion of a shell material, or rotational molding. In one embodiment, the step of forming the flexible shell comprises forming a shell with an opening and the process further includes attaching a patch to cover the opening. The patch may be an unvulcanized elastomer and is attached prior to the step of curing. Alternatively, the step of forming the flexible shell comprises forming a shell with an opening and the process further includes attaching valve, for example, a one-way valve to cover the opening. The rounded salt crystals may comprise sodium chloride.

A further understanding of the nature and advantages of the present invention are set forth in the following description and

BRIEF DESCRIPTION OF THE DRAWINGS

Features and advantages of the present invention will become appreciated and the same become better understood with reference to the specification, claims, and appended drawings wherein:

DETAILED DESCRIPTION

The present invention provides a saline- or gel-filled soft implant for prostheses and tissue expanders. The implant generally comprises a shell, for example, a silicone elastomer shell, with a textured surface. The primary application for such soft implants is to reconstruct or augment the female breast. Other potential applications are implants for the buttocks, testes, or calf, among other body regions.

Figure 1C:
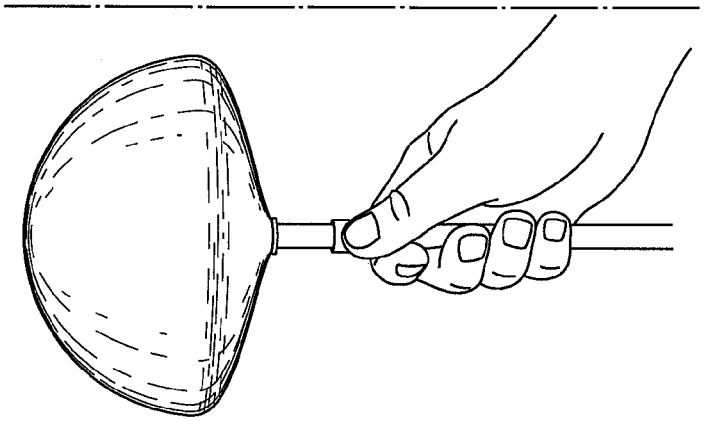
FIGS. 1A-1C show several steps in a process of dip-forming the shell of a breast implant prosthesis.
Figure 1B:
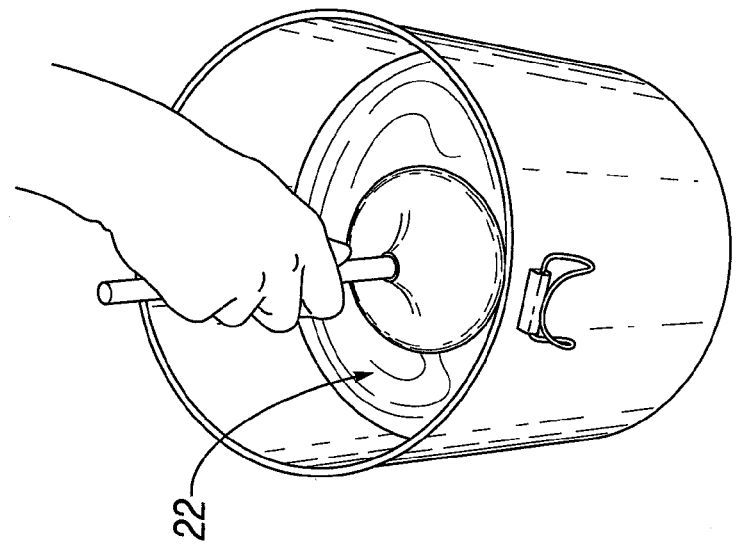
Figure 1A:
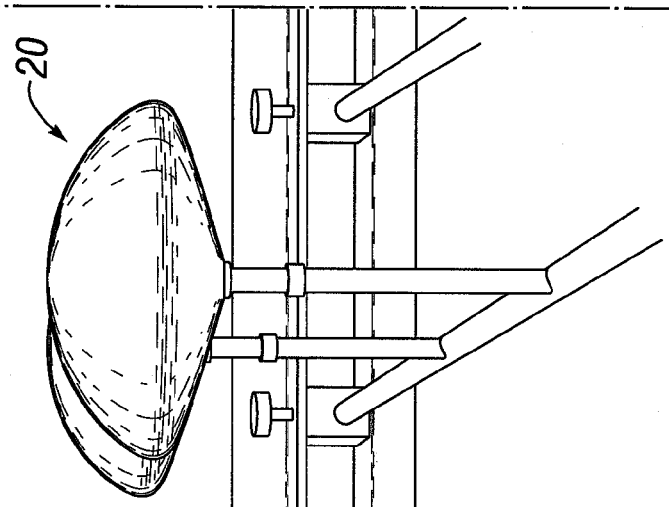

FIGS. 1A-1C illustrate one process for forming flexible implant shells for implantable prostheses and tissue expanders, involving dipping a suitably shaped mandrel 20 into a silicone elastomer dispersion 22. Many such dispersions are used in the field. Basically they contain a silicone elastomer and a solvent. The silicone elastomer is typically polydimethylsiloxane, polydiphenyl-siloxane or some combination of these two elastomers. Typical solvents include xylene or trichloromethane. Different manufacturers vary the type and amount of the ingredients in the dispersion, the viscosity of the dispersion and the solid content of the dispersion. Nonetheless, the present invention is expected to be adaptable to have utility with a wide variety of silicone rubber dispersions.

The mandrel 20 is withdrawn from the dispersion and the excess silicone elastomer dispersion is allowed to drain from the mandrel. After the excess dispersion has drained from the mandrel at least a portion of the solvent is allowed to volatilize or evaporate. Normally this is accomplished by flowing air over the coated mandrel at a controlled temperature and humidity. Different manufacturers use various quantities, velocities or directions of air flow and set the temperature and humidity of the air at different values. However, the desired result, driving off the solvent, remains the same.

It is also common for prostheses manufacturers to repeat this dip and volatilize procedure a number of times so that a number of layers are built up on the mandrel to reach a desired shell thickness. A layered structure like most current silicone elastomer shells can be made by sequentially dipping the mandrel in different dispersions. Alternatively, the steps may be repeated in a single dispersion 22 so that the finished product is a single homogenous material or layer. That is, the dipping process may be done in multiple stages or steps, each step adding more material, yet the finished product exhibits no distinct layers and the entire shell wall is homogenous or uniform in composition.

Figure 2:
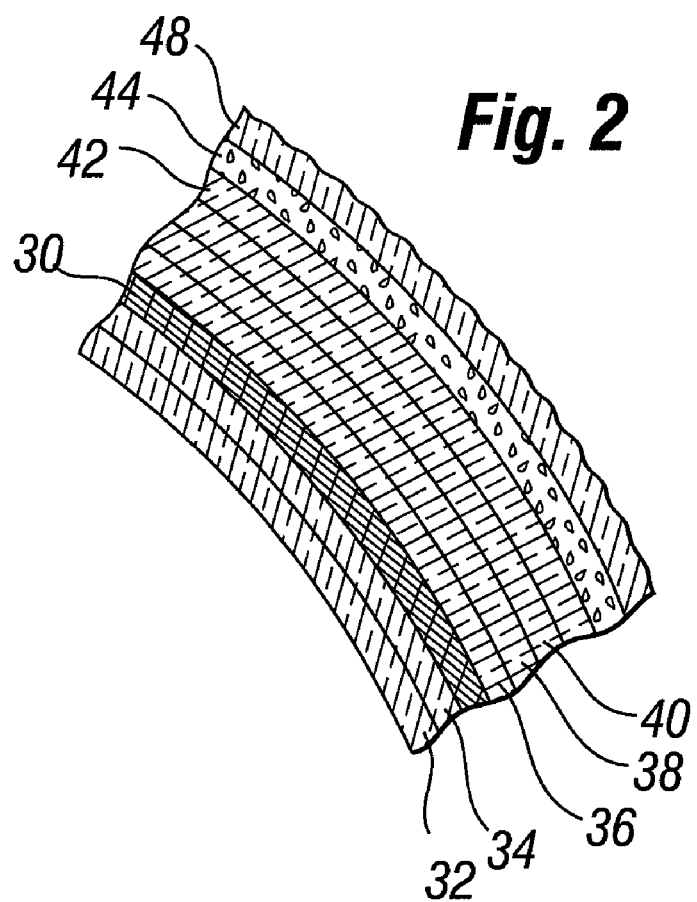
FIG. 2 is a cross-sectional view through one portion of a textured multi-layered breast implant prosthesis shell.

FIG. 2 illustrates in cross-section a portion of a textured multi-layered implant of the present invention. A primary barrier to fluid passage through the shell wall is provided by an inner barrier layer 30. Two base coat layers 32, 34 lie radially inward from the barrier layer 30. In some cases a single base coat layer may be used. On the outer side of the barrier layer 30, three further base coat layers 36, 38, 40 are provided, although again a single outer layer may be used. Furthermore, outside of the outer base coat layers 30-40, a tack coat layer 42, a layer of textured crystals 44, and an overcoat layer 48 are provided. The absolute thickness of the implant wall may vary but an exemplary average thickness is about 0.456 mm (0.018inches). The overall thickness of the textured implant wall is somewhat greater than a similar smooth-walled shell because of the extra layers.

Figure 3:
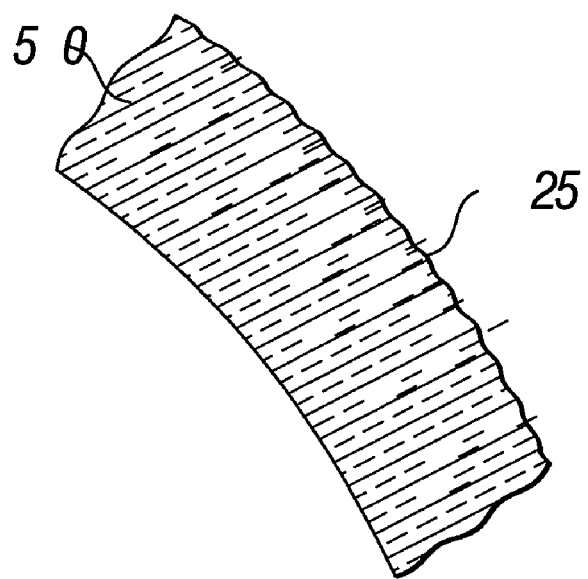
FIG. 3 is a cross-sectional view through one portion of a textured single-layer breast implant prosthesis shell.

Alternatively, FIG. 3 illustrates a cross-section of textured single-layered implant shell wall 50 that is a homogeneous silicone elastomer made entirely of a barrier material that sterically retards permeation of the silicone gel through the shell. The outer surface 52 of the barrier layer 50 is textured. The implants made with the single layer 50 may be for implant in the breast such that the entire flexible outer shell is shaped accordingly, for instance in with a more flattened posterior side and rounded anterior side.

In addition to the aforementioned dipping process, the flexible shell for the prosthetic implant may be formed using a molding process. For example, a rotational molding process such as described in Schuessler, U.S. Pat. No. 6,602,452, may be used. The process for forming texturing on the exterior surface is preferably done using a dipping technique, but the formation of the flexible shell may then be accomplished by one of a number of methods.

An exemplary process for forming a textured outer surface on either a multi-layered shell as in FIG. 2 or a single-layered shell as in FIG. 3 will now be described. After the mandrel 20 of FIGS. 1A-1C is raised out of the dispersion with what is to be the final layer adhering thereto, this layer is allowed to stabilize. That is, it is held until the final coating no longer flows freely. This occurs as some of the solvent evaporates from the final coating, raising its viscosity.

Again, it should be understood that alternative methods are contemplated for forming the flexible shell prior to the texturing process. The dip molding process advantageously results in the flexible shell pre-mounted on a dipping mandrel, which can then be used for the texturing process. However, if the flexible shell is made by another technique, such as by rotational molding, it can subsequently be mounted on a dipping mandrel and the process continued in the same manner.

Once the flexible shell has been stabilized and mounted on the mandrel, any loose fibers or particles are blown off of the exterior of the shell with an anti-static air gun. A tack coat layer is then applied. The tack coat layer may be sprayed on, or may be applied by dipping the flexible shell on the mandrel into a tack coat material, for example, a tack coat dispersion. The operator immerses the flexible shell into the dispersion and returns the mandrel to a rack for stabilization. The time required for stabilization typically varies between about 5 and about 20 minutes. A suitable tack coat layer may be made using the same material employed in the base layers.

After tack coat layer has been applied, rounded salt particles are applied substantially evenly over the entire surface. The solid particles may be applied manually by sprinkling them over the surface while the mandrel is manipulated, or a machine operating like a bead blaster or sand blaster could be used to deliver a steady stream of solid particles at an adequate velocity to the coating on the mandrel.

In one embodiment, the coated mandrel is dipped into a body of the particles. In another embodiment, particle application is accomplished by exposing the coated mandrel to a liquid dispersion of the particles. It should be understood that the present invention is not intended to be restricted to any one particular method of applying the particles.

In one embodiment, a salt bath for coating the tacky flexible shells is prepared by first procuring a quantity of rounded salt crystals and sorting the crystals into a desired size range. For example, unsorted rounded salt crystals are placed in a shaker having a first sieve size (e.g. coarse sieve) and a second sieve size (e.g. fine sieve). Larger salt crystals will be stopped by the coarse sieve at the inlet of the salt shaker, while smaller salt crystals will continue through both of the sieves. Crystals in the desired size range are trapped between the sieves. In a specific embodiment, the first sieve is a 14 mesh sieve and the second sieve is a 20 mesh sieve. In another embodiment, the first sieve is a 20 mesh sieve and the second sieve is a 40 mesh sieve. In yet another embodiment, the first sieve is a 40 mesh sieve and the second sieve is a 80 mesh sieve.

In one embodiment, the rounded particles used in accordance with the invention have a substantially uniform particle size of between about 150 microns and about 1450 microns.

In one embodiment, the rounded particles comprise or consist of relatively fine grained particles. For example, in one embodiment, the rounded particles have a maximum particle size of at least about 150 microns, for example, the particles have a maximum particle size in a range of between about 180 microns and about 425 microns. For example, about 90% of the rounded particles will be retained between a sieve having mesh size 80 and a sieve having mesh size 40.

In another embodiment, the rounded particles comprise or consist of relatively medium grained particles. For example, in one embodiment, the rounded particles have a maximum particle size of at least about 300 microns, for example, the particles have a maximum particle size in a range of between about 425 microns and about 850 microns. For example, about 90% of the particles will be retained between a sieve having mesh size 40 and a sieve having mesh size 20.

In yet another embodiment, the rounded particles comprise or consist of relatively large grained particles. For example, in one embodiment, the rounded particles have a maximum particle size of at least about 800 microns, for example, the particles have a maximum particle size in a range of between about 850 microns and about 1450 microns. For example, about 90% of the particles will be retained between a sieve having mesh size 20 and a sieve having mesh size 14.

The size of the salt crystals can be selected by sorting a bulk quantity of rounded salt crystals using a series of gradually smaller meshes.

In accordance with one embodiment of the invention, the salt crystals, for example, those having a particular size distribution are then added to an aqueous salt bath prior to being applied to the shell. The tacky flexible shells are immersed in the salt bath, rotated for even coverage, removed, and then allowed to stabilize. After a suitable period of stabilization, such as between about 5 minutes and about 20 minutes, the flexible shells may be dipped into an overcoat dispersion. A suitable overcoat dispersion may also be made using the same material employed in the base layers. The flexible shells on the mandrels are then mounted on a rack and allowed to volatilize for a sufficient time, such as, for example, about 15 minutes.

In one embodiment, the entire silicone elastomer shell structure is vulcanized or cured in an oven at elevated temperatures. For example, the temperature of the oven is maintained at a temperature between about 200° F. and about 350° F. for a curing time preferably between about 20 minutes and about 1 hour, 40 minutes.

Upon removal from the oven, the mandrel/shell assembly is placed in a solvent for the solid particles, and the solid particles are allowed to dissolve. The solvent is a material that does not affect the structure or integrity of the silicone elastomer. When the solid particles have dissolved, the assembly is removed from the solvent and the solvent evaporated. The shell is then removed from the mandrel. At this point, it is preferable to place the shell in a solvent for the solid particles and gently agitate it to ensure complete dissolution of all the solid particles. Once the shell has been removed from the solvent, the solvent evaporates or otherwise is removed from the shell.

Dissolving the solid particles leaves behind open pores, voids or spaces in the surface of the shell. When applied, some of the solid particles are partially exposed so that they can be acted upon by the solvent. These exposed solid particles also provide a way for the solvent to reach those solid particles beneath the surface to dissolve them in turn. The result is an interconnected structure of cells, some of which are open to the surface, in the outer layer of the shell. The process described above produces a shell like that shown in either FIG. 2 or 3. The shell has a thin outer wall made of silicone elastomer with an opening therein at the point where a support member connected to the mandrel 20, which opening will subsequently be covered with a patch.

Figure 4:
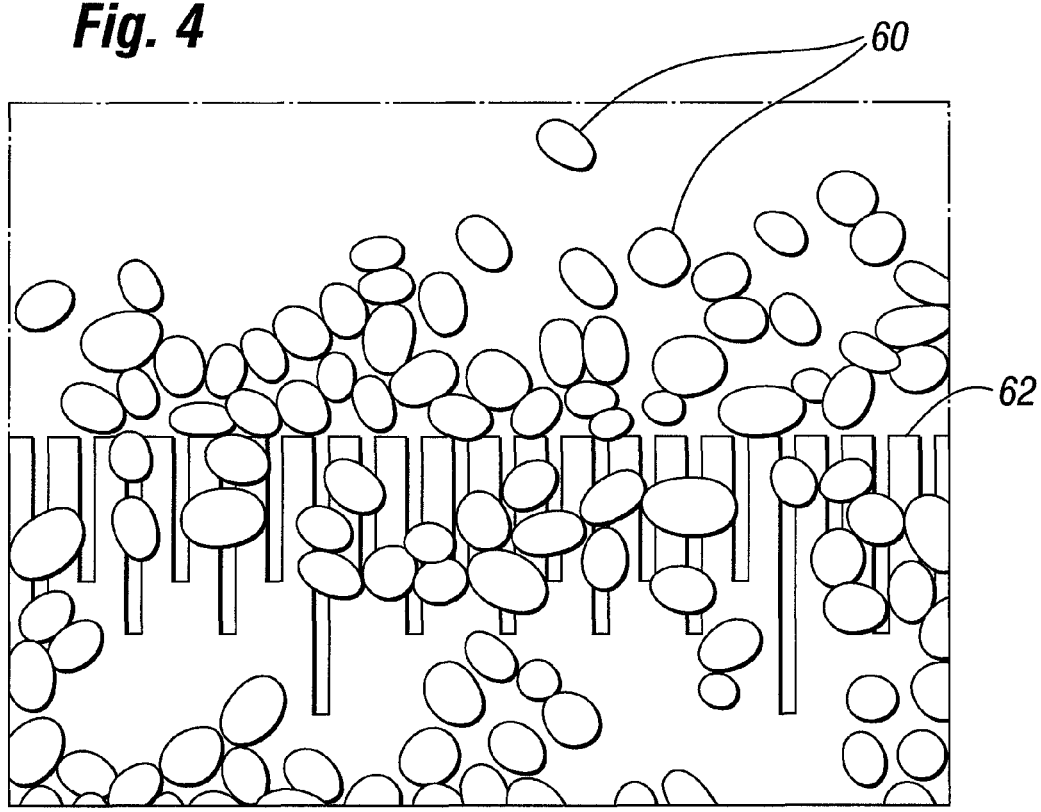
FIG. 4 is a magnified view of a sample of rounded salt crystals used in the implant texturing process of the present invention.
Figure 5:
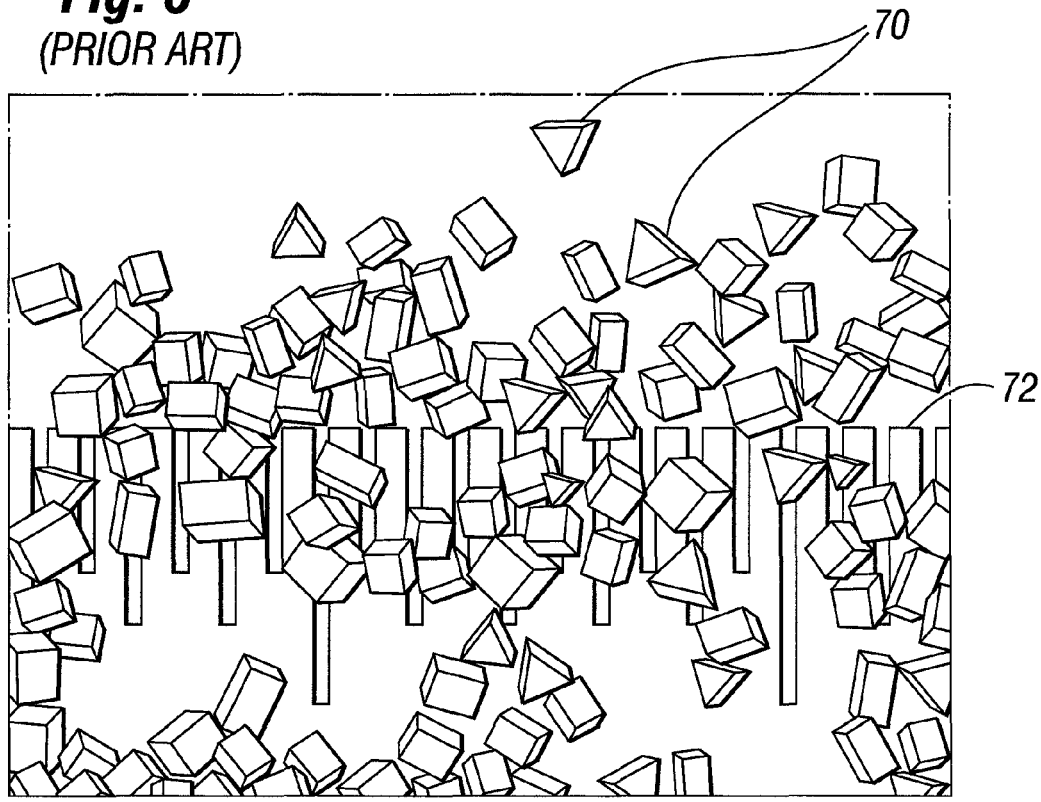
FIG. 5 is a magnified view of a sample of cubic salt crystals used in conventional implant texturing processes of the prior art.

The present invention diverges from previous processes in the make-up of the salt crystals used in the dispersion 22. Namely, as seen in FIG. 4, rounded salt crystals 60 are shown over a reference scale 62. In contrast to regular crystalline sodium chloride 70, as seen against a scale 72 in FIG. 5, the rounded salt crystals 60 have been appropriately processed to smooth any sharp or non-rounded edges that are typically found on standard sodium chloride crystals 70 (sometimes, termed "cubic salt crystals").

Figure 6A:
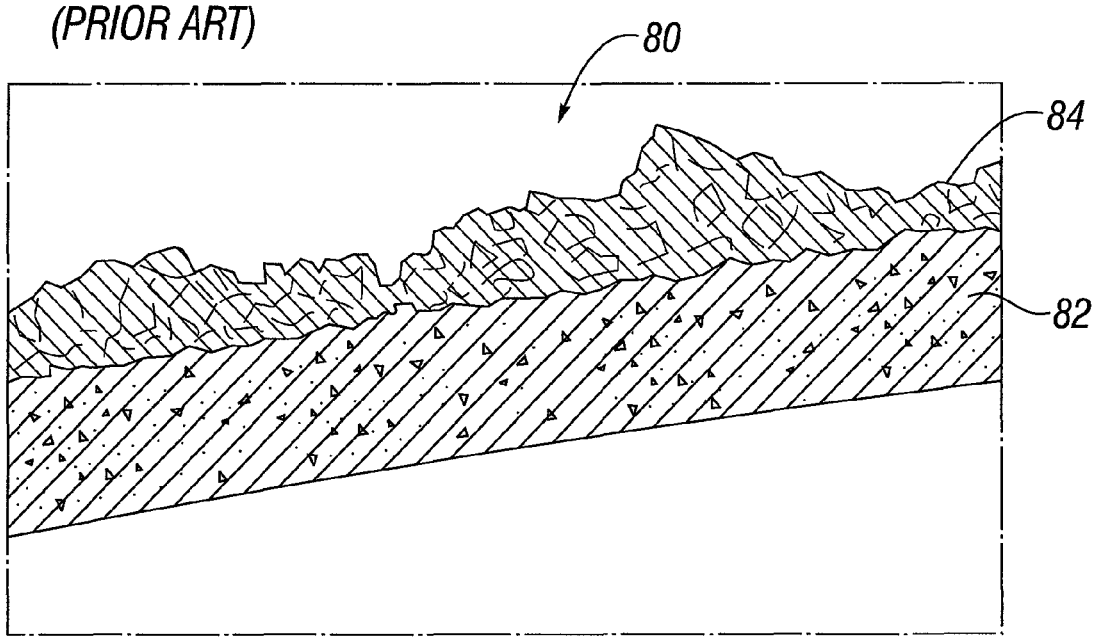
FIGS. 6A and 6B are cross-sectional and plan views, respectively, of a textured implant of the prior art.
Figure 6B:
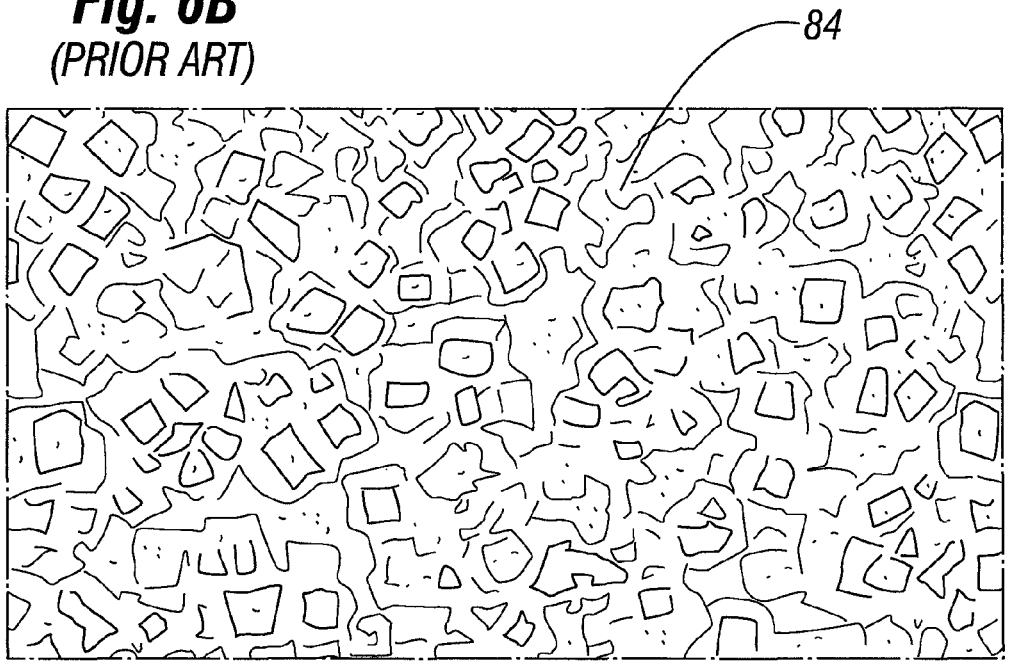

FIGS. 6A and 6B illustrate in magnified cross-section and plan view, respectively, an implant shell 80 of the prior art having texturing formed using conventional cubic salt crystals. The shell 80 includes an inner wall 82 and an outer textured surface 84. This textured surface 84 is formed by applying cubic salt crystals and then dissolving those crystals to leave an open-celled porous surface. The relatively rough surface 84 is partly the result of the angular salt crystals used in the formation process. The particular texture illustrated is sold under the tradename Biocell® surface texture by Allergan, Inc. of Irvine, Calif.

Figure 7A:
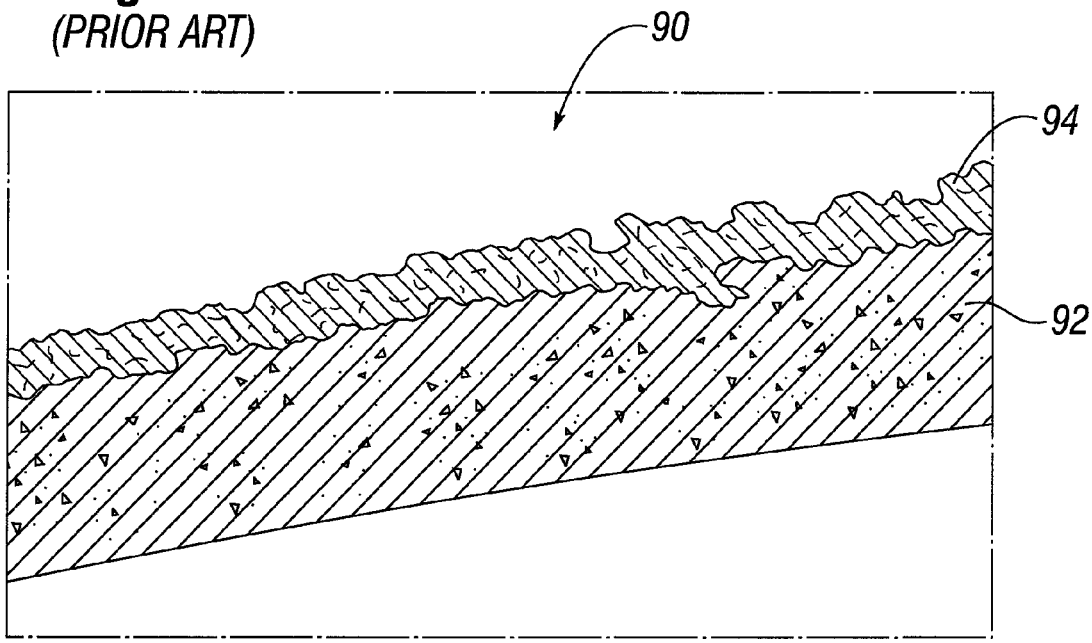
FIGS. 7A and 7B are cross-sectional and plan views, respectively, of another textured implant of the prior art.
Figure 7B:
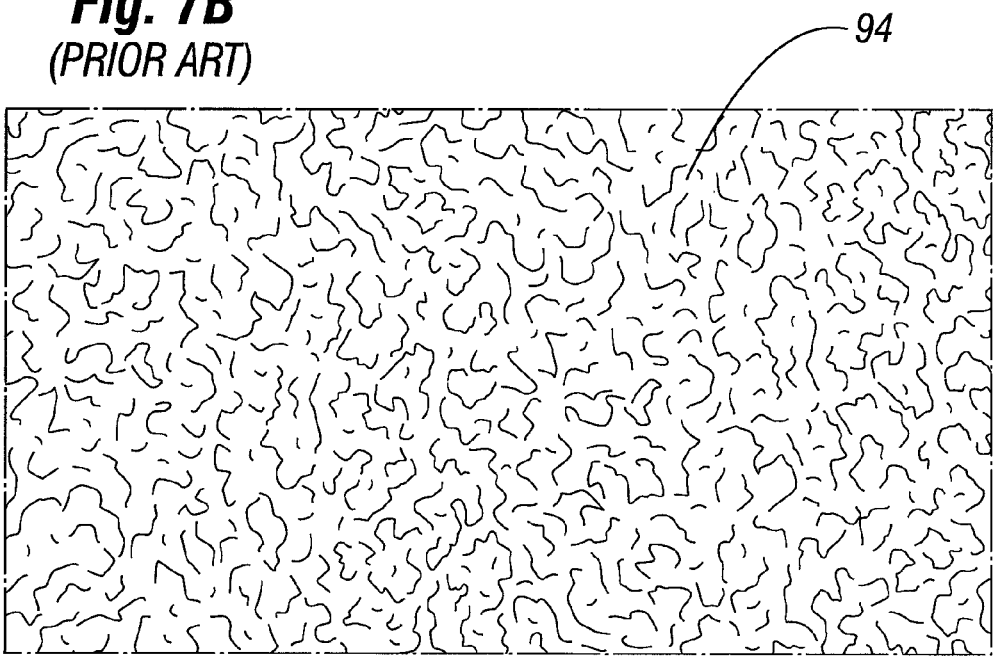

FIGS. 7A and 7B illustrate in magnified cross-section and plan view, respectively, another implant shell 90 of the prior art having texturing formed using conventional cubic salt crystals. The shell 90 includes an inner wall 92 and an outer textured surface 94. This textured surface 94 is formed by an embossing process that imprints the texture on uncured silicone material. The particular texture illustrated is sold under the tradename Siltex® surface texture by Mentor Corp. of Santa Barbara, Calif.

Figure 8A:
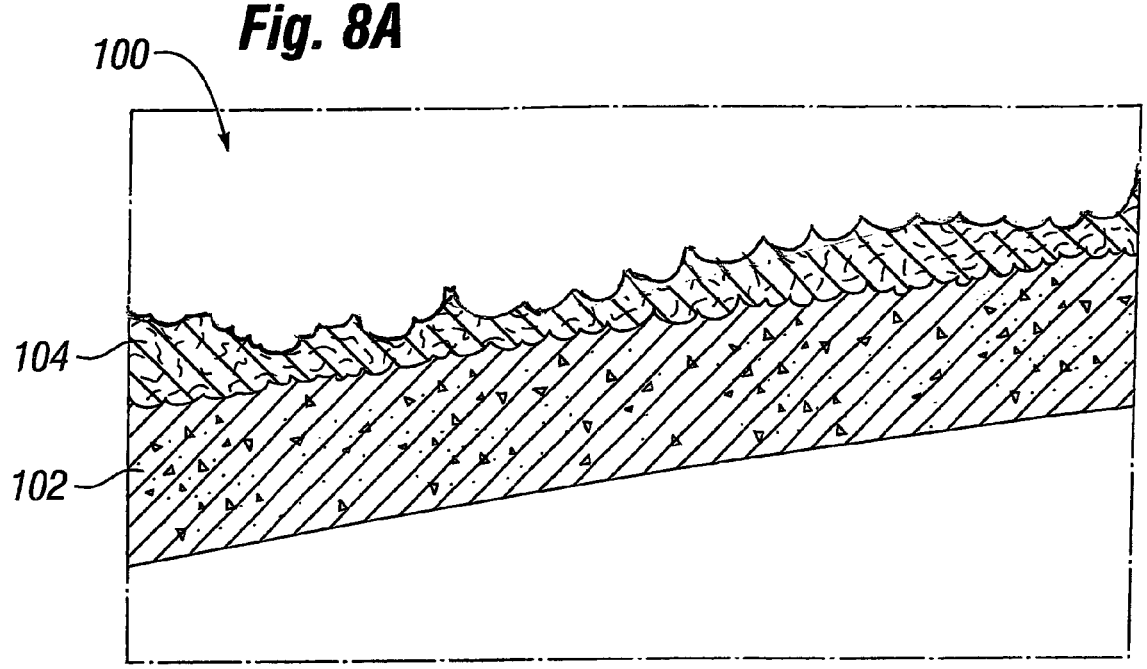
FIGS. 8A and 8B are cross-sectional and plan views, respectively, of a textured implant in accordance with the present invention.
Figure 8B:
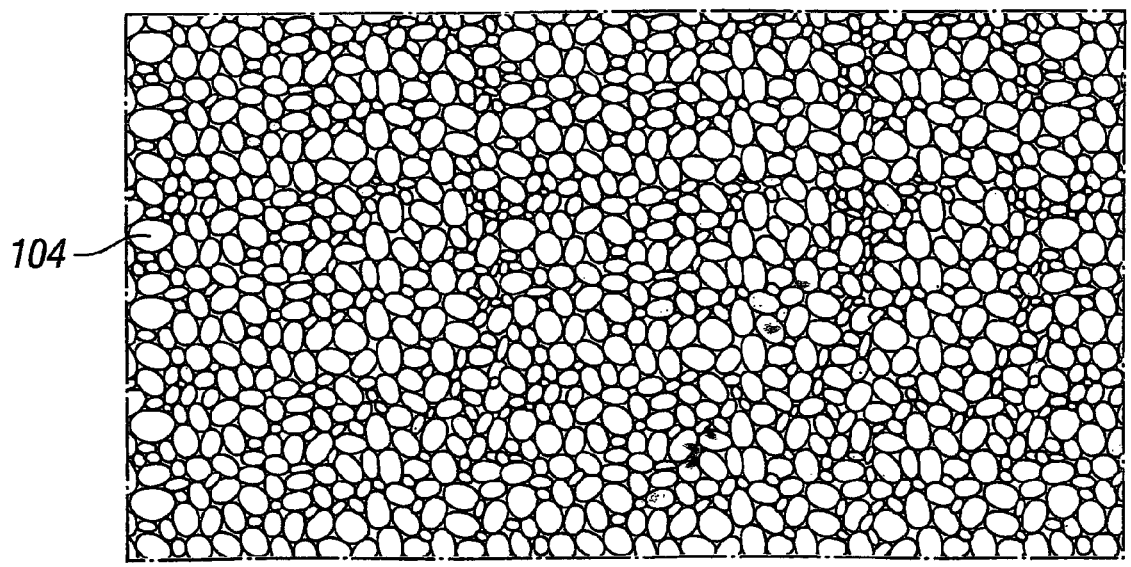

Now with references to FIGS. 8A and 8B, a magnified cross-section and plan view of an implant shell 100 of the present invention having texturing formed using rounded salt crystals is illustrated. The shell 100 includes an inner wall 102 and an outer textured surface 104 exhibiting an undulating topography. This textured surface 104 is formed by applying rounded salt crystals and then dissolving those crystals to leave an open-celled, porous, textured surface, as explained above. The textured surface 104 is somewhat smoother than those made with angular salt crystals, as seen in FIGS. 6 and 7. Although not shown in great detail, the pores or openings in the open-celled surface 104 have smoother dividing walls and fewer angular discontinuities than the pores or openings in conventionally manufactured shells that are otherwise identical but use angular salt crystals rather than rounded salt crystals. As will be shown, this difference surprisingly leads to statistically significant changes in overall shell strength.

In one embodiment, the rounded salt crystals are applied so as to achieve a depth ranging from a portion of one crystal diameter to a multiple of many crystal diameters. The crystals may be embedded in the surface of the shell to a depth of from about one to about three times the diameter of the crystals. Penetration of the solid crystals depends upon the size of the crystals, the thickness of the final uncured layer, the viscosity of the uncured layer and the force with which the crystals are applied. These parameters can be controlled to achieve a desired depth of penetration. For example, if the last layer is relatively thick and low in viscosity, less external force will be required on the solid crystals to produce an acceptable pore depth.

Although standard sodium chloride is preferably used for the rounded salt crystals, other salts may be suitable based on several factors: (1) the salt should be economically available in the desired particle sizes; (2) the salt should be nontoxic in case some remains in the surface of the prosthesis; and (3) the salt should be readily soluble in a solvent that is economically available, nontoxic and does not dissolve the silicone elastomer.

In one embodiment, the rounded salt particles are sodium chloride crystals which are readily available in granulated form, and can be processed into round crystals, for example, by an industrial milling facility, including Central Salt & Marine Chemicals Research Institute of Bhavnagar, India, a subsidiary of the Council of Scientific & Industrial Research (CSIR), a publicly funded industrial R&D organization in India. When crystalline sodium chloride is used in accordance with the invention, the solvent may comprise pure water. A person of ordinary skill in the art will understand that a number of solid and solvent pairs could be chosen in accordance with various embodiments of the invention.

After finishing the shell according to the steps described above, additional processing steps may be performed. For example, the opening left by the dip molding process may be patched with unvulcanized sheeting, for example, uncured silicone elastomer sheeting. If the prosthesis is to be filled with silicone gel, this gel may be added and cured, the filled prosthesis packaged, and the packaged prosthesis sterilized. If the prosthesis is to be inflated with a saline solution, a one-way valve is assembled and installed, the prosthesis is post cured if required, and the prosthesis is then cleaned, packaged and sterilized. A combination breast implant prosthesis can also be made wherein a gel-filled sac is positioned inside the shell to be surrounded by saline solution.

As mentioned above, the properties of an implant shell having a texture formed with round salt crystals are statistically superior to those formed using cubic salt crystals. This is believed to be due to a reduction in stress concentrations, which may be seen at the sharp corners formed using cubic salt crystals.

To compare the different shells, standard tensile strength specimens were cut from the shells and subjected to stress tests. The comparison shell was a standard commercial textured shell of the prior art sold under the tradename INAMED® BIOCELL® Saline- or Silicone-Filled Breast Implants, by Allergan, Inc. of Irvine, Calif. More specifically, random BIOCELL® shells formed using the process described with reference to FIGS. 6A and 6B were used for comparison. Sixty specimens from this group were cut using an H2 die and tested for tensile strength. Table I below illustrates the results.

TABLE I

Test of Prior Art Commercial Textured Shells

| | Thickness | Stress@ % elongation (psi) | | | | Ultimate Break force | Ultimate Elongation | Tensile Strength |
|---|---|---|---|---|---|---|---|---|
| | (in) | 50% | 100% | 200% | 300% | (lbf) | (%) | (psi) |
| Mean | 0.0209 | 52.79 | 84.40 | 176.119 | 295.552 | 4.272 | 621.690 | 819.079 |
| Std. | 0.0021 | 3.54 | 5.79 | 11.985 | 19.723 | 0.511 | 32.227 | 42.482 |
| Min | 0.0170 | 44.49 | 70.49 | 147.73 | 250.188 | 3.439 | 552.016 | 752.760 |
| Max | 0.0260 | 63.89 | 102.77 | 213.868 | 355.503 | 5.802 | 707.647 | 912.512 |

Likewise, sixty specimens from a group of shells formed using the process of the present invention were cut using an H2 die and tested for tensile strength. Table II below illustrates the results.

TABLE II

Test of Shells Produced with Process of the Present Invention

| | Thickness | Stress@ % elongation (psi) | | | | Ultimate Break force | Ultimate Elongation | Tensile Strength |
|---|---|---|---|---|---|---|---|---|
| | (in) | 50% | 100% | 200% | 300% | (lbf) | (%) | (psi) |
| Mean | 0.0214 | 47.50 | 76.08 | 163.350 | 280.964 | 4.494 | 662.411 | 841.880 |
| Std. | 0.0013 | 2.18 | 3.74 | 7.811 | 12.474 | 0.328 | 20.845 | 33.806 |

TABLE II-continued

Test of Shells Produced with Process of the Present Invention

| | Thickness | Stress@ % elongation (psi) | | | | Ultimate Break force | Ultimate Elongation | Tensile Strength |
|---|---|---|---|---|---|---|---|---|
| | (in) | 50% | 100% | 200% | 300% | (lbf) | (%) | (psi) |
| Min | 0.0190 | 42.52 | 68.33 | 147.318 | 252.912 | 3.617 | 591.457 | 761.376 |
| Max | 0.0250 | 52.20 | 84.29 | 179.215 | 305.826 | 5.528 | 705.347 | 934.60 |

These data show that test samples of similar thickness formed by the methods of the present invention experience lower stresses during elongation while the break force, ultimate elongation, and tensile strengths are significantly higher. Specifically, the mean thickness of the test samples formed in accordance with present invention was 0.0214 inches, while the mean thickness of the prior art test samples was 0.0209 inches, or around a 2.3% difference. However, the mean ultimate break force for samples of the present invention was more than 5% greater, the mean ultimate elongation was more than 6% greater, and the mean ultimate tensile strength was nearly 3% greater than samples of the prior art. Given the number of samples (n=60), these differences are somewhat surprising given the similar technique for forming the shells and similar thicknesses. Applicants believe that the rounded salt crystals form a smoother open-cell structure on the exterior of the shells which reduces stress concentrations. As such, the test results indicate other than an expected linear relationship proportional to the difference in thickness.

It is also important to note the improvement in ultimate elongation. The resulting 662% mean elongation for the sixty shells tested is well past the level required by various regulatory bodies around the word. In particular, the U.S. standard is 350% from ASTM F703, Standard Specification for Implantable Breast Prostheses. In Europe and elsewhere, the standard for elongation is set at 450% by ISO 14607. The implant shells formed by the lost material technique and rounded salt crystals satisfy these standards with greater margins of confidence than ever before. It is believed that changing from a cubic crystal with sharp corners and edges to the rounded crystals where stress concentrations are more evenly distributed helps statistically meet consensus performance breast standards.

In addition, tests were conducted on shells that were formed using the texturing process of the present invention both with conventional cubic salt crystals and with the rounded salt crystals disclosed herein. That is, instead of comparing the shells of the present invention with existing commercial shells, new shells were formed using the same process but with conventional angular or cubic salt crystals. Specifically, five shells textured with regular cubic salt crystals were dip molded, and five shells textured with rounded salt crystals were also dip molded. All the shells were subjected to gel curing at 145° C. for 8 hours, and then subjected to a simulated sterilization at 127° C. for 20.5 hours. Sixty tensile strength specimens from each batch were cut with an H2 die and tested. These results are shown in the following Tables III and IV.

TABLE III

Test of Textured Shells formed with Cubic Salt Crystals

| | Thickness | Stress@ % elongation (psi) | | | Ultimate Break force | Ultimate Elongation | Tensile |
|---|---|---|---|---|---|---|---|
| | (in) | 100% | 200% | 300% | (lbf) | (%) | Strength (psi) |
| Mean | 0.0197 | 108.44 | 245.196 | 427.548 | 3.157 | 574.394 | 1020.331 |
| Std. | 0.0012 | 4.32 | 9.455 | 15.716 | 0.253 | 22.905 | 50.407 |
| Min | 0.017 | 96.59 | 218.531 | 396.776 | 2.73 | 513.924 | 905.827 |
| Max | 0.022 | 119.34 | 270.61 | 471.472 | 3.781 | 616.102 | 1126.053 |

TABLE IV

Test of Textured Shells formed with Rounded Salt Crystals

| | Thickness | Stress@ % elongation (psi) | | | Ultimate Break force | Ultimate Elongation | Tensile |
|---|---|---|---|---|---|---|---|
| | (in) | 100% | 200% | 300% | (lbf) | (%) | Strength (psi) |
| Mean | 0.0196 | 113.49 | 253.224 | 437.177 | 3.321 | 593.298 | 1076.807 |
| Std. | 0.0015 | 5.13 | 10.537 | 16.966 | 0.337 | 22.248 | 57.867 |
| Min | 0.015 | 102.42 | 232.879 | 401.088 | 2.189 | 543.156 | 926.505 |
| Max | 0.025 | 124.49 | 276.015 | 473.083 | 4.321 | 639.847 | 1181.189 |

Again, these data show that test samples of similar thickness formed by the methods of the present invention experience lower stresses during elongation while the break force, ultimate elongation, and tensile strengths are significantly higher. Specifically, the mean thickness of the test samples formed in accordance with present invention was 0.0196 inches, while the mean thickness of the prior art test samples was 0.0197 inches, or around a 0.05% difference, with the samples made in accordance with the present invention being thinner on average. However, the mean ultimate break force for samples of the present invention was more than 5% greater, the mean ultimate elongation was more than 3% greater (and sufficient to meet global standards), and the mean ultimate tensile strength was nearly 6% greater than samples of the prior art. Given the number of samples (n=60) and the fact that the shells were identically formed except for the shape of the salt crystals, these differences are even more surprising than the previous comparison. Once again, the test results indicate a non-linear relationship relative to the difference in thickness.

Although the invention has been described and illustrated with a certain degree of particularity, it is understood that the present disclosure has been made only by way of example, and that numerous changes in the combination and arrangement of parts can be resorted to by those skilled in the art without departing from the scope of the invention, as hereinafter claimed.

What is claimed is:

1. A soft prosthetic breast implant, formed by a process comprising:
    forming a flexible shell of silicone elastomer, the silicone elastomer having a thickness;
    adhering on the exterior of the flexible shell an even distribution of round particles;
    curing the flexible shell with the round particles adhered thereto; and
    removing the round particles thereby forming an open-pored structure on the exterior of the flexible shell such that the exterior of the flexible shell exhibits an undulating topography, the open pored-structure comprising round open cavities defined by impressions of the round particles;
    processing the flexible shell such that it forms a closed envelope;
    wherein the flexible shell formed by the process has at least one of the physical properties of ultimate break force, ultimate elongation, or ultimate tensile strength that is superior to such physical property of an identical flexible shell made using the same process and same materials except for angular particles instead of round particles;
    wherein the round particles have a substantially uniform particle size within a particle size range selected from a group of ranges consisting of (1) a range between 180 microns and 425 microns, (2) a range between 425 microns and 850 microns, and (3) a range between 850 microns and 1450 microns; and
    wherein the open-pored structure does not extend through the entire thickness of the silicone elastomer.

2. The breast implant of claim 1, wherein the particles are round salt particles.

3. The breast implant of claim 1, wherein the step of forming the flexible shell comprises dipping a mandrel into a liquid dispersion of an elastomeric material.

4. The breast implant of claim 3, wherein the step of forming the flexible shell comprises rotationally molding the shell.

5. The breast implant of claim 3, wherein the round particles are sodium chloride crystals.

6. The breast implant of claim 1 wherein the ultimate break force of the flexible shell is more than 5% greater than the ultimate break force of said identical flexible shell made using the same process and same materials except for angular particles instead of round particles.

7. The breast implant of claim 1 wherein the ultimate elongation of the flexible shell is more than 6% greater than the ultimate elongation of said identical flexible shell made using the same process and same materials except for angular particles instead of round particles.

8. The breast implant of claim 1 wherein the ultimate tensile strength of the flexible shell is 3% greater than an ultimate tensile strength of said identical flexible shell made using the same process and same materials except for angular particles instead of rounded round particles.

9. The breast implant of claim 1 wherein about 90% of the round particles are in the selected particle size range.

10. The breast implant of claim 1 wherein the selected particle size range is the range between 850 microns and 1450 microns.

11. The breast implant of claim 1 wherein the selected particle size range is the range between 425 microns and 850 microns.

12. The breast implant of claim 1 wherein the selected particle size range is the range between 180 microns and 425 microns.

* * * * *

UNITED STATES PATENT AND TRADEMARK OFFICE
CERTIFICATE OF CORRECTION

| | | |
|---|---|---|
| PATENT NO. | : 8,313,527 B2 | Page 1 of 1 |
| APPLICATION NO. | : 12/261939 | |
| DATED | : November 20, 2012 | |
| INVENTOR(S) | : Thomas E. Powell et al. | |

It is certified that error appears in the above-identified patent and that said Letters Patent is hereby corrected as shown below:

In the Claims

In column 12, line 35, in claim 8, delete "rounded round" and insert -- round --, therefor.

Signed and Sealed this
Thirtieth Day of September, 2014

Michelle K. Lee
*Deputy Director of the United States Patent and Trademark Office*